United States Patent [19]

Hsiao et al.

[11] Patent Number: 4,755,386

[45] Date of Patent: Jul. 5, 1988

[54] BUCCAL FORMULATION

[75] Inventors: Chiin H. Hsiao, Cooper City; Janice L. Cacace, Hollywood, both of Fla.

[73] Assignee: Schering Corporation, Kenilworth, N.J.

[21] Appl. No.: 821,358

[22] Filed: Jan. 22, 1986

[51] Int. Cl.⁴ ............................................... A61K 9/20
[52] U.S. Cl. ..................................... 424/435; 424/78; 424/80; 424/81; 514/778; 514/779; 514/781
[58] Field of Search ................... 424/78, 81, 80, 435; 514/778, 779, 781

[56] References Cited

U.S. PATENT DOCUMENTS

| | | | |
|---|---|---|---|
| 4,059,686 | 11/1977 | Tanaka et al. | 424/435 |
| 4,226,848 | 10/1980 | Nagai et al. | 424/435 |
| 4,292,299 | 9/1981 | Suzuki et al. | 424/435 |
| 4,572,832 | 2/1986 | Kigasawa et al. | 424/435 |

FOREIGN PATENT DOCUMENTS 1380171  1/1975  United Kingdom .

OTHER PUBLICATIONS

Kornblum et al., (II) J. Pharm. Sci. 62(1): 43–49, Jan. 1973.
Khan et al., (I), Mfg. Chemist: 25–26, Jan. 1976.
Khan et al., (II), J. Pharm. Pharmac. 28: 633–636 (1976).

Primary Examiner—Shep K. Rose
Attorney, Agent, or Firm—Richard C. Billups; James R. Nelson; Stephen I. Miller

[57] ABSTRACT

A buccal formulation for administering a medicament includes about 1–20% by weight of a soluble, pharmaceutically acceptable adhesive, about 1–10% by weight of a pharmaceutically acceptable disintegrant and a soluble, directly compressible tablet excipient.

15 Claims, No Drawings

BUCCAL FORMULATION

BACKGROUND OF THE INVENTION

This application is directed to a formulation for the buccal administration of an active ingredient. Buccal administration (in the pouch of the cheek of the subject) is particularly useful for active ingredients which show poor bioavailability upon administration through other non-parenteral modes. This poor availability can be attributed to low solubility, degradation by enzyme or destruction by acid upon passing through the intestinal tract, or first pass destruction by the liver after absorption from the gastrointestinal tract. Examples of such medicaments include: steroids such as estrogens, e.g. estradiol and derivatives such as the salt and valerate, cypionate or propionate forms; progestins, e.g. progesterone and related compounds, androgens and anabolic steroids; propranolol; thyroid hormones; pH sensitive peptides and small proteins such as insulin and ACTH; physostigmine; scopolamine; verapamil; and gallopamil. It is also possible to administer compounds having good oral bioavailability buccally, but normally such medicaments would be administered orally for convenience.

Buccal administration of estradiol gives an early peak in the blood level followed by decreasing concentration. This tracks the natural occurrence of estradiol in the body, and thus is an improvement over transdermal administration, which provides a relatively constant blood level. Oral administration of estrogens such as estradiol is impractical in view of the destruction of the active ingredient in the liver shortly after absorption from the gastrointestinal tract.

It is necessary for a buccal formulation to remain in contact with the oral mucosa for a time sufficient for absorption of the medicament to be administered. If the formulation falls apart too quickly. the active ingredient is swallowed, and an insufficient amount of medicament is delivered. If the formulation does not fall apart quickly enough, patient compliance difficulties can result, since the patient should not eat or drink while using the buccal formulation. The formulation should be of a small size to avoid discomfort to the patient and it is desirable that as much of the formulation as possible be soluble in saliva so that discomfort in the form of insoluble grit in the mouth can be avoided.

SUMMARY OF THE INVENTION

In a first aspect, this invention is directed to a buccal composition for administration of a medicament, comprising: about 1 to about 20% by weight of a soluble, pharmaceutically acceptable polymeric adhesive; about 1 to about 10% by weight of a pharmaceutically acceptable table disintegrant; a soluble, directly compressible table excipient; and a therapeutically useful amount of medicament.

According to a further aspect, this invention is directed to a buccal composition for administration of an estrogen, comprising about 2 to about 10% by weight of carbomer 934 P; about 3 to about 6% by weight crospovidone; sugar; and about 50 micrograms to 2 mg of estradiol.

DETAILED DESCRIPTION OF THE INVENTION

According to the present invention, a useful buccal formulation includes four components: a soluble, pharmaceutically acceptable polymeric adhesive; a pharmaceutically acceptable disintegrant; a soluble, directly compressible tablet excipient; and active ingredient.

The soluble, pharmaceutically acceptable polymeric adhesive is used to provide tackiness to the buccal formulation so that it will be held in place upon administration. The amount of adhesive in the formulation is about 1-20% by weight, preferably about 2-10%. Use of amounts less than 1% may result in insufficient adhesive properties or the formulation falling apart too quickly, while excessive amounts may result in the formulation lasting for a longer period than is desirable. The adhesives desirably are sticky when moist, but not when dry, for convenience in handling. The amount of adhesive which can be used increases with the solubility of the active ingredient.

One particularly desirable group of adhesives are high molecular weight polymers of acrylic acid known as carbomers. Molecular weights of 450,000 to 4,000,000 are useful, with a molecular weight of about 3,000,000 (carbomer 934 P) being preferred. These substances are sold by B. F. Goodrich under the trademark Carbopol ®. The adhesives have been found to allow use of minimal amounts to provide the desired adhesive characteristics to the formulation, which is advantageous since increasing amounts of adhesive may impede the dissolution of the active ingredient. Other suitable hydrophilic polymers include partially (87-89%, for example) hydrolyzed polyvinylalcohol (molecular weight 10,000 to 125,000, preferably 11,000 to 31,000), polyethylene oxide (molecular weight about 100,000 to about 5,000,000, preferably 400,000) and polyacrylates, such as that sold by GAF under the trademark Gantrez ®, particularly those designated as high molecular weight polyacrylates. Hydroxypropyl methylcellulose, having a molecular weight of 13,000 to 140,000 (sold under the trademark Methocel ® by Dow), and hydroxypropyl cellulose, having a molecular weight of 60,000 to 1,000,000 (sold under the trademark Klucel ®) also are useful adhesives. Material toward the high end of each of the molecular weight ranges are preferred. The term "soluble" is used throughout this application as an indication that the material is soluble in water or saliva.

Upon administration, the adhesive forms a gel-like substance which is gradually broken up by a pharmaceutically acceptable disintegrant which swells upon administration, thus exposing more of the formulation to saliva. This causes the formulation to break up gradually. The amount of disintegrant in the formulation is about 1 to 10% by weight, preferably 3-6%. Excessive amounts of disintegrant actually may unduly delay disintegration, as by formulation of an insoluble gel, instead of aiding dissolution of the formulation by expansion. One useful disintegrant is the material crospovidone, which is a cross-linked polyvinylpyrrolidone product. This material is sold under the trademark Polyplasdone XL by GAF. Other useful disintegrants include Ac-di-sol ® (FMC's trademark for croscarmellose, a cross-linked carboxylic methylcellulose), alginic acid and sodium carboxymethyl starch such as that sold as Explotab ® by Edward Mendell Co., Inc.

The formulation also includes a soluble, directly compressible tableting excipient such as a sugar. One such useful tableting excipient is a co-crystallization of 97% sucrose-3% highly modified dextrins sold under the trademark Di-Pac ® by Amstar. Other such excipients known to those skilled in the art, such as lactone, also may be used. The amount of excipient used is such that the resulting formulation is big enough to be handled conveniently, yet small enough to dissolve properly. Other ingredients which may be used include lubricants such as magnesium stearate in the amount of up to about 1% by weight, preferably 0.5%, and coloring or flavoring agents.

The active ingredients useful with this invention include those mentioned in the Background of the Invention. Of course, the amount will vary depending upon the dosage desired for a given treatment. Estradiol, when used as the active ingredient, is present in the amount of about 50 micrograms to 2 mg.

The formulations of the present invention can be prepared by simply mixing the ingredients together and compressing desired amounts of the mixture into tablet form. The final formulations desirably have a diameter of about a quarter inch (0.635 cm) and a thickness of about 0.05 inches (0.127 cm), and upon administration disintegrate in about 2–20 minutes, preferably about 4–12 minutes.

The present invention is illustrated by the following non-limiting examples.

EXAMPLE 1

The following ingredients are charged into a blender and mixed for ten minutes.

| % BY WEIGHT | INGREDIENT | AMOUNT |
| --- | --- | --- |
| 0.2 | Estradiol, USP (Micronized) | 2.0 g |
| 89.3 | Di-Pac (Compressible Sugar, NF) | 893.0 g |
| 5.0 | Carbomer 934P, NF (Carbopol ® 934P) | 50.0 g |
| 5.0 | Crospovidone, NF (Polyplasdone ® XL) | 50.0 g |
| 0.5 | Magnesium Stearate, NF | 5.0 g |
| 100.0 | | 1,000.0 g |

Tablets weighing about 0.05 gm./tablet are formed using a compression force of about 1000 PSI. The batch yields about 20,000 tablets which upon administration disintegrate in about 10–15 minutes. The tablets are about ¼ inch in diameter.

EXAMPLE 2

Following the procedures of Example 1, the following is mixed and formed into tablets.

| % BY WEIGHT | INGREDIENT | AMOUNT |
| --- | --- | --- |
| 0.4 | Estradiol, USP (Micronized) | 4.0 g |
| 89.0 | Di-Pac (Compressible Sugar, NF) | 890.0 g |
| 5.0 | Carbomer 934P, NF (Carbopol ® 934P) | 50.0 g |
| 5.0 | Crospovidone, NF (Polyplasdone ® XL) | 50.0 g |
| 0.5 | Magnesium Stearate, NF | 5.0 g |
| 0.1 | FDC Yellow #6 Lake | 1.0 g |
| 100.0 | | 1,000.0 g |

Results similar to those of Example 1 are obtained.

Although a detailed description has been provided above, the present invention is not limited thereto, but rather is defined in the following claims.

What is claimed is:

1. A buccal composition for administration of an active ingredient comprising;
   (a) about 1 to about 20% by weight of a soluble, pharmaceutically acceptable polymeric adhesive;
   (b) about 1 to about 10% by weight of a pharmaceutically acceptable table disintegrant;
   (c) a soluble, directly compressible table excipient; and
   (d) a therapeutically useful amount of active ingredient.

2. The composition of claim 1, wherein said adhesive is selected from the group consisting of a carbomer, partially hydrolyzed polyvinyl alcohol, polyethylene oxide, polyacrylate, hydroxypropyl methylcellulose and hydroxypropyl cellulose.

3. The composition of claim 2, wherein the adhesive is a carbomer.

4. The composition of claim 3, wherein the adhesive is carbomer 934 P.

5. The composition of claim 1, wherein said disintegrant is selected from the group consisting of crospovidone, cross-linked carboxylic methylcellulose, alginic acid and sodium carboxymethyl starch.

6. The composition of claim 5, wherein said disintegrant is cross-linked polyvinylpyrrolidone.

7. The composition of claim 1, wherein the amount of adhesive is about 2 to about 10% by weight.

8. The composition of claim 1, wherein the amount of disintegrant is about 3 to about 6% by weight.

9. The composition of claim 1, wherein said excipient is a sugar.

10. The composition of claim 1, wherein said active ingredient is selected from the group consisting of an estrogen, a progestin, an androgen, an anabolic steroid, propranolol, insulin, ACTH, physostigmine, scopolamine, verapamil, and gallopamil.

11. The composition of claim 10, wherein the active ingredient is estradiol or a pharmaceutically acceptable derivative thereof.

12. The composition of claim 11, wherein the amount of estradiol is about 50 micrograms to 2 mg.

13. A buccal composition for administration of an estrogen, comprising:
   (a) about 2 to about 10% by weight of carbomer 934P;
   (b) about 3 to about 6% by weight crospovidone;
   (c) sugar; and
   (d) a therapeutically useful amount of an estrogen.

14. The composition of claim 13, wherein the estrogenis estradiol, in the amount of about 50 micrograms to 2 mg.

15. A buccal composition for transmucosal administration of an effective amount of an active ingredient comprising:
   (a) about 1 to about 20% by weight of a soluble, pharmaceutically acceptable polymeric adhesive;
   (b) about 1 to about 10% by weight of a pharmaceutically acceptable table disintegrant admixed with said polymeric adhesive;
   (c) a soluble, directly compressible table excipient, and
   (d) a therapeutically useful amount of an active ingredient.

* * * * *

UNITED STATES PATENT AND TRADEMARK OFFICE
CERTIFICATE OF CORRECTION

PATENT NO. : 4,755,386
DATED : July 5, 1988
INVENTOR(S) : Chiin H. Hsiao and Janice L. Cacace It is certified that error appears in the above-identified patent and that said Letters Patent are hereby corrected as shown below:

On page 1, col. 1, after "Assignee:", delete Schering Corporation, Kenilworth, N.J. and insert -- Key Pharmaceuticals, Inc., Miami, Fla.

Signed and Sealed this

Tenth Day of January, 1989

Attest:

DONALD J. QUIGG

Attesting Officer

Commissioner of Patents and Trademarks